US009670538B2

(12) United States Patent
Huff et al.

(10) Patent No.: US 9,670,538 B2
(45) Date of Patent: Jun. 6, 2017

(54) NUCLEIC ACID SEQUENCING BY ELECTROCHEMICAL DETECTION

(75) Inventors: Jeffrey Huff, Lincolnshire, IL (US); Graham Davis, Princeton, NJ (US); Mark Hayden, Ingleside, IL (US); David J. Ecker, Encinitas, CA (US); Dan Wang, Ottawa (CA); Gordon Bruce Collier, Fitzroy Harbour (CA)

(73) Assignee: IBIS BIOSCIENCES, INC., Carlsbad, CA (US)

( * ) Notice: Subject to any disclaimer, the term of this patent is extended or adjusted under 35 U.S.C. 154(b) by 639 days.

(21) Appl. No.: 14/237,328

(22) PCT Filed: Aug. 3, 2012

(86) PCT No.: PCT/US2012/049585
§ 371 (c)(1),
(2), (4) Date: May 12, 2014

(87) PCT Pub. No.: WO2013/022778
PCT Pub. Date: Feb. 14, 2013

(65) Prior Publication Data
US 2014/0238859 A1    Aug. 28, 2014

Related U.S. Application Data

(60) Provisional application No. 61/515,673, filed on Aug. 5, 2011.

(51) Int. Cl.
*G01N 27/327*   (2006.01)
*C12Q 1/68*     (2006.01)
*G01N 27/447*   (2006.01)
*G01N 27/333*   (2006.01)

(52) U.S. Cl.
CPC ....... *C12Q 1/6869* (2013.01); *G01N 27/3275* (2013.01); *G01N 27/333* (2013.01); *G01N 27/447* (2013.01); *G01N 27/44756* (2013.01)

(58) Field of Classification Search
CPC .......................... G01N 27/3275; G01N 27/333
See application file for complete search history.

(56) References Cited

U.S. PATENT DOCUMENTS

| | | |
|---|---|---|
| 4,613,422 A | 9/1986 | Lauks |
| 4,739,380 A | 4/1988 | Lauks et al. |
| 4,933,048 A | 6/1990 | Lauks |
| 5,009,766 A | 4/1991 | Lauks |
| 5,063,081 A | 11/1991 | Cozzette et al. |
| 5,096,669 A | 3/1992 | Lauks et al. |
| 5,198,093 A * | 3/1993 | Sydlowski ......... G01N 27/4165 204/406 |
| 5,200,051 A | 4/1993 | Cozzette et al. |
| 5,447,440 A | 9/1995 | Davis et al. |
| 5,628,961 A | 5/1997 | Davis et al. |
| 5,695,934 A | 12/1997 | Brenner |
| 5,714,330 A | 2/1998 | Brenner et al. |
| 5,750,341 A | 5/1998 | Macevicz |
| 5,804,971 A * | 9/1998 | Cumming ............ G01N 27/286 204/406 |
| 5,821,399 A | 10/1998 | Zelin |
| 5,837,446 A | 11/1998 | Cozzette et al. |
| 5,837,454 A | 11/1998 | Cozzette et al. |
| 5,912,148 A | 6/1999 | Eggerding |
| 6,030,827 A | 2/2000 | Davis et al. |
| 6,130,073 A | 10/2000 | Eggerding |
| 6,210,891 B1 | 4/2001 | Nyren et al. |
| 6,258,568 B1 | 7/2001 | Nyren |
| 6,306,597 B1 | 10/2001 | Macevicz |
| 6,379,883 B2 | 4/2002 | Davis et al. |
| 6,432,360 B1 | 8/2002 | Church |
| 6,485,944 B1 | 11/2002 | Church et al. |
| 6,511,803 B1 | 1/2003 | Church et al. |
| 6,750,053 B1 | 6/2004 | Widrig Opalsky et al. |
| 6,787,308 B2 | 9/2004 | Balasubramanian et al. |
| 6,818,395 B1 | 11/2004 | Quake et al. |

(Continued)

FOREIGN PATENT DOCUMENTS

| | | |
|---|---|---|
| WO | WO-8909283 A1 | 10/1989 |
| WO | WO-9323564 A1 | 11/1993 |
| WO | WO-9828440 A1 | 7/1998 |
| WO | WO-0018957 A1 | 4/2000 |
| WO | WO-2006084132 A2 | 8/2006 |
| WO | WO 2012/042399 A1 * | 4/2012 ........... G01N 27/414 |

OTHER PUBLICATIONS

Palumbo et al., "The Simple Fool's Guide to PCR version 2.0," pp. 1-45, Oct. 29, 2002.*
Adessi C., et al., "Solid Phase DNA Amplification: Characterisation of Primer Attachment and Amplification Mechanisms," Nucleic Acids Research, 2000, vol. 28 (20), pp. E87.
Alderborn A., et al., "Determination of Single-nucleotide Polymorphisms by Real-time Pyrophosphate DNA Sequencing," Genome Research, 2000, vol. 10 (8), pp. 1249-1258.
Astier Y., et al., "Toward Single Molecule DNA Sequencing: Direct Identification of Ribonucleoside and Deoxyribonucleoside 5'-monophosphates by Using an Engineered Protein Nanopore Equipped with a Molecular Adapter," Journal of the American Chemical Society, 2006, vol. 128 (5), pp. 1705-1710.

(Continued)

*Primary Examiner* — Alexander Noguerola
(74) *Attorney, Agent, or Firm* — David A. Casimir; Casimir Jones, S.C.

(57) ABSTRACT

Provided herein is technology relating to sequencing nucleic acids and particularly, but not exclusively, to devices, methods, and systems for sequencing-by-synthesis using changes in pH to monitor base addition. In some embodiments the electrochemical hydrogen ion sensor is a microfabricated mixed metal oxide electrode and in some embodiments the electrochemical hydrogen ion sensor is a membrane electrode. Moreover, in some embodiments the device further comprises a reference electrode. Performing the sequencing reaction involves moving solutions and other fluids (e.g., samples, nucleotide solutions, wash solutions) into and out of the reaction vessel. Thus, in some embodiments, the device further comprises a tube or other transport mechanism or pathway attached to the reaction vessel.

20 Claims, No Drawings

(56) References Cited

U.S. PATENT DOCUMENTS

| | | | |
|---|---|---|---|
| 6,833,246 B2 | 12/2004 | Balasubramanian | |
| 6,911,345 B2 | 6/2005 | Quake et al. | |
| 6,969,488 B2 | 11/2005 | Bridgham et al. | |
| 7,115,400 B1 | 10/2006 | Adessi et al. | |
| 7,169,560 B2 | 1/2007 | Lapidus et al. | |
| 7,170,050 B2 | 1/2007 | Turner et al. | |
| 7,282,337 B1 | 10/2007 | Harris | |
| 7,302,146 B2 | 11/2007 | Turner et al. | |
| 7,313,308 B2 | 12/2007 | Turner et al. | |
| 7,315,019 B2 | 1/2008 | Turner et al. | |
| 7,329,492 B2 | 2/2008 | Hardin et al. | |
| 7,348,783 B1* | 3/2008 | Hsiung | G01N 27/4167 324/438 |
| 7,405,281 B2 | 7/2008 | Xu et al. | |
| 7,419,821 B2 | 9/2008 | Davis et al. | |
| 7,476,503 B2 | 1/2009 | Turner et al. | |
| 7,482,120 B2 | 1/2009 | Buzby | |
| 7,501,245 B2 | 3/2009 | Quake et al. | |
| 7,540,948 B2 | 6/2009 | Collier et al. | |
| 7,723,099 B2 | 5/2010 | Miller et al. | |
| 7,932,034 B2 | 4/2011 | Esfandyarpour et al. | |
| 2002/0090738 A1 | 7/2002 | Cozzette et al. | |
| 2004/0023253 A1* | 2/2004 | Kunwar | C12Q 1/003 435/6.11 |
| 2005/0032075 A1* | 2/2005 | Yaku | C12Q 1/6858 435/6.16 |
| 2005/0130173 A1 | 6/2005 | Leamon et al. | |
| 2007/0009944 A1 | 1/2007 | Bowater et al. | |
| 2007/0036511 A1 | 2/2007 | Lundquist et al. | |
| 2007/0072196 A1 | 3/2007 | Xu et al. | |
| 2007/0077564 A1 | 4/2007 | Roitman et al. | |
| 2007/0128133 A1 | 6/2007 | Eid et al. | |
| 2007/0134128 A1 | 6/2007 | Korlach | |
| 2007/0141598 A1 | 6/2007 | Turner et al. | |
| 2007/0161017 A1 | 7/2007 | Eid et al. | |
| 2007/0188750 A1 | 8/2007 | Lundquist et al. | |
| 2007/0196846 A1 | 8/2007 | Hanzel et al. | |
| 2007/0206187 A1 | 9/2007 | Lundquist et al. | |
| 2007/0231804 A1 | 10/2007 | Korlach et al. | |
| 2007/0238679 A1 | 10/2007 | Rank et al. | |
| 2008/0009007 A1 | 1/2008 | Lyle et al. | |
| 2008/0030628 A1 | 2/2008 | Lundquist et al. | |
| 2008/0032301 A1 | 2/2008 | Rank et al. | |
| 2008/0050747 A1 | 2/2008 | Korlach et al. | |
| 2008/0080059 A1 | 4/2008 | Dixon et al. | |
| 2008/0095488 A1 | 4/2008 | Foquet et al. | |
| 2008/0108082 A1 | 5/2008 | Rank et al. | |
| 2008/0128627 A1 | 6/2008 | Lundquist et al. | |
| 2008/0145278 A1 | 6/2008 | Korlach | |
| 2008/0152280 A1 | 6/2008 | Lundquist et al. | |
| 2008/0152281 A1 | 6/2008 | Lundquist et al. | |
| 2008/0153095 A1 | 6/2008 | Williams et al. | |
| 2008/0153100 A1 | 6/2008 | Rank et al. | |
| 2008/0157005 A1 | 7/2008 | Lundquist et al. | |
| 2008/0160531 A1 | 7/2008 | Korlach | |
| 2008/0165346 A1 | 7/2008 | Lundquist et al. | |
| 2008/0176241 A1 | 7/2008 | Eid et al. | |
| 2008/0176316 A1 | 7/2008 | Eid et al. | |
| 2008/0176769 A1 | 7/2008 | Rank et al. | |
| 2008/0199874 A1 | 8/2008 | Otto et al. | |
| 2008/0199932 A1 | 8/2008 | Hanzel et al. | |
| 2008/0206764 A1 | 8/2008 | Williams et al. | |
| 2008/0212960 A1 | 9/2008 | Lundquist et al. | |
| 2009/0026082 A1 | 1/2009 | Rothberg et al. | |
| 2009/0035777 A1 | 2/2009 | Kokoris et al. | |
| 2009/0127589 A1 | 5/2009 | Rothberg et al. | |
| 2010/0137143 A1 | 6/2010 | Rothberg et al. | |
| 2010/0167938 A1 | 7/2010 | Su et al. | |
| 2010/0188073 A1 | 7/2010 | Rothberg et al. | |
| 2010/0197507 A1 | 8/2010 | Rothberg et al. | |
| 2010/0301398 A1 | 12/2010 | Rothberg et al. | |
| 2011/0171655 A1 | 7/2011 | Esfandyarpour et al. | |

OTHER PUBLICATIONS

Bains W., et al., "A Novel Method for Nucleic Acid Sequence Determination," Journal of Theoretical Biology, 1988, vol. 135 (3), pp. 303-307.

Bennett S.T., et al., "Toward the 1,000 Dollars Human Genome," Pharmacogenomics, 2005, vol. 6 (4), pp. 373-382.

Birren B., et al., eds., Genome Analysis—A Laboratory Manual, vol. 1, Cold Spring Harbor Laboratory Press, 1997, Table of Contents.

Brenner S., et al., "Gene Expression Analysis by Massively Parallel Signature Sequencing (MPSS) on Microbead Arrays," Nature Biotechnology, 2000, vol. 18 (6), pp. 630-634.

Co-pending U.S. Appl. No. 11/671,956, filed Feb. 6, 2007.

Co-pending U.S. Appl. No. 11/781,166, filed Jul. 20, 2007.

Co-pending U.S. Appl. No. 61/481,592, filed May 2, 2011.

Driscoll R.J., et al., "Atomic-scale Imaging of DNA Using Scanning Tunnelling Microscopy," Nature, 1990, vol. 346 (6281), pp. 294-296.

Hyman E.D., "A New Method of Sequencing DNA," Analytical Biochemistry, 1988, vol. 174 (2), pp. 423-436.

International Search Report and Written Opinion for Application No. PCT/US2012/049585, mailed on Nov. 6, 2012, 12 pages.

Jett J.H., et al., "High-speed DNA Sequencing: an Approach Based Upon Fluorescence Detection of Single Molecules," Journal of Biomolecular Structure & Dynamics, 1989 , vol. 7 (2), pp. 301-309.

Korlach J., et al., "Selective Aluminum Passivation for Targeted Immobilization of Single DNA Polymerase Molecules in Zero-Mode Waveguide Nanostructures," Proceedings of the National Academy of Sciences, 2008, vol. 105 (4), pp. 1176-1181.

MacLean D., et al., "Application of 'next-generation' Sequencing Technologies to Microbial Genetics," Nature Reviews Microbiology, 2009, vol. 7 (4), pp. 287-296.

Margulies M., et al., "Genome Sequencing in Microfabricated High-Density Picolitre Reactors," Nature, 2005, vol. 437 (7057), pp. 376-380.

Mitra R.D., et al., "Fluorescent in Situ Sequencing on Polymerase Colonies," Analytical Biochemistry, 2003, vol. 320 (1), pp. 55-65.

Morozova O., et al., "Applications of Next-generation Sequencing Technologies in Functional Genomics," Genomics, 2008, vol. 92 (5), pp. 255-264.

Pennisi E., "Genomics. Semiconductors Inspire New Sequencing Technologies," Science, 2010, vol. 327 (5970), pp. 1190.

Ronaghi M., et al., "A sequencing method based on real-time pyrophosphate," Science, 1998, vol. 281 (5375), pp. 363-365.

Seo T.S., et al., "Four-color DNA Sequencing by Synthesis on a Chip Using Photocleavable Fluorescent Nucleotides," Proceedings of the National Academy of Sciences of the United States of America, 2005, vol. 102 (17), pp. 5926-5931.

Shendure J., et al., "Accurate Multiplex Polony Sequencing of an Evolved Bacterial Genome," Science, 2005, vol. 309 (5741), pp. 1728-1732.

Voelkerding K.V., et al., "Next-Generation Sequencing: from Basic Research to Diagnostics," Clinical Chemistry, 2009, vol. 55 (4), pp. 641-658.

* cited by examiner

```
                         SEQUENCE LISTING

<160> NUMBER OF SEQ ID NOS: 3

<210> SEQ ID NO 1
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-5AmMC6

<400> SEQUENCE: 1
tttttttttt tttttttttt agttatgcaa cgcgggagtt gtgtatgaag t            51

<210> SEQ ID NO 2
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
tgcatgcaac ttcatacaca actcccgcgt tgcataact                          39

<210> SEQ ID NO 3
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gcatgcatac ttcatacaca actcccgcgt tgcataact                          39
```

NUCLEIC ACID SEQUENCING BY ELECTROCHEMICAL DETECTION

CROSS-REFERENCE TO RELATED APPLICATION

The present Application claims priority to U.S. Provisional Application Ser. No. 61/515,673 filed Aug. 5, 2011, the entirety of which is herein incorporated by reference.

FIELD OF INVENTION

Provided herein is technology relating to sequencing nucleic acids and particularly, but not exclusively, to devices, methods, and systems for sequencing-by-synthesis using changes in pH to monitor base addition.

BACKGROUND

DNA sequencing is an essential tool in molecular genetic analysis. The ability to determine DNA nucleotide sequences has become increasingly important as an integral component of many medical diagnostics. Historically, the two most commonly used methods for DNA sequencing were the enzymatic chain-termination method of Sanger and the chemical cleavage technique of Maxam and Gilbert. Both methods rely on gel electrophoresis to resolve, according to their size, DNA fragments produced from a larger DNA segment. Since the electrophoresis step as well as the subsequent detection of the separated DNA-fragments were cumbersome procedures, many efforts had been made to develop more efficient sequencing methods, for example, by developing novel technologies that do not use electrophoresis. Research efforts have produced several such techniques including, e.g., sequencing using scanning tunnel electron microscopy (see, e.g., Driscoll et al., *Nature* 346: 294-96 (1990)), sequencing by hybridization (see e.g., Bains et al., *J. Theo. Biol.* 135: 308-07 (1988)), and single molecule detection (Jeff et al., *Biomol. Struct. Dynamics* 7: 301-06 (1989)), to overcome the disadvantages of gel electrophoresis.

In addition, some efforts focused on methods of sequencing based on the concept of detecting the inorganic pyrophosphate (PP) that is released during a DNA polymerase reaction (e.g., as described in WO 93/23564 and WO 89/09283; see Seo et al. "Four-color DNA sequencing by synthesis on a chip using photocleavable fluorescent nucleotides," *PNAS* 102: 5926-59 (2005); Hyman, "New method of sequencing DNA" *Anal. Biochem.* 174: 423-36 (1988)). In these "sequencing by synthesis" methods, as each nucleotide is added to a growing nucleic acid strand during a polymerase reaction, the released pyrophosphate molecule is detected. It has been found that pyrophosphate released under these conditions can be detected enzymatically, e.g., in some applications by the generation of light in the luciferase-luciferin reaction. Such methods allow a user to sequence DNA simply and rapidly whilst avoiding the need for electrophoresis and the use of harmful radiolabels. In addition, these methods have found use in identifying single target bases, e.g., in the mapping of single nucleotide polymorphisms.

One of the first sequencing by synthesis methods was "Pyrosequencing™", which was developed at the Royal Institute of Technology in Stockholm (see Nyren, "Method for sequencing DNA based on the detection of the release of pyrophosphate and enzymatic nucleotide degradation", U.S. Pat. No. 6,258,568 (2001); WO 98/28440; Ronaghi, et al. *Science* 281: 363 (1998); Alderborn et al., (2000), each incorporated herein by reference in their entireties for all purposes). The method, in contrast to conventional Sanger sequencing, adds nucleotides one by one during the sequencing reaction. In some implementations the principle is as follows: A single stranded DNA fragment (attached to a solid support), carrying an annealed sequencing primer acts as a template for the reaction. In the first two dispensations, substrate and enzyme mixes are added to the template. The enzyme mix consists of four different enzymes; DNA polymerase, ATP-sulfurylase, luciferase and apyrase. The nucleotides are sequentially added one by one according to a specified order dependent on the template and determined by the user. If the added nucleotide matches the template, the DNA polymerase incorporates it into the growing DNA strand and $PP_i$ is released. The ATP-sulfurylase converts the $PP_i$ into ATP, and the third enzyme, luciferase, transforms the ATP into a light signal. Following these reactions, the fourth enzyme, apyrase, degrades the excess nucleotides and ATPs, and the template is ready for the next reaction cycle, i.e. another nucleotide addition. Since no $PP_i$ is released unless a nucleotide is incorporated, a light signal is produced only when the correct nucleotide is incorporated.

In a related method, the incorporation of a nucleotide during sequencing-by-synthesis is detected by a change in the heat or pH of the reaction solution (see, e.g., U.S. Pat. No. 7,932,034). In one implementation of these methods, a template strand having an attached primer is immobilized in a small volume reaction mixture, with the reaction mixture in contact with a sensitive calorimeter, which detects the heat of reaction from incorporation of a complementary base (dNTP) in the presence of appropriate reagents (DNA polymerase, and polymerase reaction buffer). Alternatively, a pH meter may be used to measure changes in pH resulting from the reaction. The bead will have template DNA attached to it, where the sequence of the template DNA molecule is the same in each of numerous strands attached to the bead, e.g., through biotin. In a known protocol, for example, 5 pg of immobilized template DNA is used. The template DNA is prepared with a known segment for attachment of a primer. In some applications, calorimetric detection is the preferred detection scheme because it allows for more sensitive detection than pH-based schemes.

In pH-based methods, pH monitoring is often performed by use of a microcantilever or a field-effect transistor (FET) sensitive to hydrogen ion concentration. In the microcantilever devices, a pH sensor with ultrahigh sensitivity was developed based on a microcantilever structure with a lithographically defined crosslinked copolymeric hydrogel. Silicon-on-insulator wafers were used to fabricate cantilevers on which a polymer consisting of poly (methacrylic acid) (PMAA) with polyethylene glycoldimethacrylate was patterned using free-radical UV polymerization. As the pH around the cantilever was increased above the $pK_a$ of PMAA, the polymer network expanded and resulted in a reversible change in surface stress causing the microcantilever to bend. These devices have a sensitivity reported to be $5 \times 10^{-4}$ pH.

In the FET devices, a chemical-sensitive FET, or more particularly an ion-sensitive FET (ISFET), is used to facilitate measurement of the hydrogen ion concentration of a solution. An ISFET is an impedance transformation device that is fabricated using conventional complementary metal oxide semiconductor (CMOS) technology, operates in a manner similar to that of a metal oxide semiconductor field effect transistor (MOSFET), and is particularly configured to selectively measure ion activity in a solution (e.g., hydrogen ion). Examples of these devices are provided, e.g., in U.S. Pat. Appl. Pub. Nos. 20090026082, 20090127589, 20100301398, 20100197507, 20100188073, and 20100137143.

Other commercially available pH meters can measure pH changes as low as 0.001. These meters contain several inputs for indicator (e.g., ion-sensitive, redox), reference electrodes, and temperature sensors such as thermoresistors or a thermocouple. The electronic pH meters typically use potentiometric methods, that is, one measures a potential difference between known reference electrode and the measuring pH electrode.

However, the sequencing methods mentioned above are not without drawbacks. For example, many methods rely on relatively sophisticated detection schemes that rely on, for example, chemiluminescence or a FET to detect the release of pyrophosphate or pyrophosphate analogues. Chemiluminescence is detected by photon counting devices and is associated with light-tight detection methods. Field effect transistors remain fairly sophisticated to fabricate and are subject to "salt effects" (e.g., Debye effects) that can inhibit the sensitivity of detection. Consequently, a need remains for a pragmatic and reliable technology for monitoring base polymerization during a sequencing by synthesis reaction.

SUMMARY

To meet this need, provided herein are methods and devices for performing a sequencing by synthesis reaction based on monitoring pH changes associated with DNA polymerization. The technology provides the sequence of one strand of DNA by synthesizing the complementary strand, one base pair at a time, and detecting the base that is incorporated at each step. Solutions of each nucleotide triphosphate—e.g., A, G, C, and T—are sequentially added to the reaction. After adding a nucleotide and checking for incorporation or non-incorporation of the nucleotide, that nucleotide solution is washed away and the next nucleotide solution is added. When the nucleotide in the solution complements the template at the next position to be incorporated to the growing strand, the nucleotide is incorporated and a proton is released among the reaction products. This proton causes a transient change in the pH of the reaction solution that can be detected. Alternatively, when a non-complementary nucleotide is added, there is no incorporation and the corresponding reaction products are not produced and there is no change in the pH. Monitoring the sequence of A, G, C, and T solutions that produce a proton (e.g., a change in the pH) at each step allows one to determine the sequence of the template.

Electrochemical sensors provide a reliable technology for a variety of sensing applications including the measurement of pH. Accordingly, provided herein is technology related to a device for determining the sequence of a nucleic acid, the device comprising a reaction vessel for containing a sample comprising the nucleic acid; and an electrochemical hydrogen ion sensor associated with the reaction vessel. In some embodiments the electrochemical hydrogen ion sensor is a microfabricated mixed metal oxide electrode and in some embodiments the electrochemical hydrogen ion sensor is a membrane electrode. Moreover, in some embodiments the device further comprises a reference electrode. Performing the sequencing reaction involves moving solutions and other fluids (e.g., samples, nucleotide solutions, wash solutions) into and out of the reaction vessel. Thus, in some embodiments, the device further comprises a tube or other transport mechanism or pathway attached to the reaction vessel.

In some embodiments, the technology is related to electrodes adapted to sense changes in hydrogen ion concentration. Electrodes can take a variety of sizes and shapes. In embodiments of the technology provided herein, the electrochemical hydrogen ion sensor in an electrode having a diameter of approximately 200 μm or less. The electrochemical hydrogen ion sensor is associated with a reaction vessel in which the sequencing reaction proceeds. As such, in some embodiments, the reaction vessel is a cylinder having a diameter of approximately 200 μm or less and a height of approximately 30 μm or less. The electrochemical hydrogen ion sensor can detect small changes in pH—in some embodiments, the electrochemical hydrogen ion sensor detects changes in pH greater than or equal to 0.1. Since most enzymatic reactions are performed in buffered conditions for proper function of the enzymes, some embodiments of the technology comprise a low ionic strength buffer to perform pH measurements. High ionic strength buffers would have the undesired effect of suppressing pH changes and compromise the usefulness of the technology. Also, some embodiments provide a device comprising a plurality of electrochemical hydrogen ion sensors.

The nucleic acid is provided in many forms. For example, in some embodiments the nucleic acid coats the surface of the electrochemical hydrogen ion sensor and in some embodiments the nucleic acid is attached to a microparticle bead. In some embodiments the nucleic acid is a single-stranded nucleic acid. A change in pH depends on the change in the concentration of hydrogen ions released into solution. Accordingly, to provide a detectable pH change, embodiments provide that the sample introduced into the device for sequencing comprises a plurality of nucleic acids that covers the electrochemical hydrogen ion sensor at a density equal to or greater than $2.2 \times 10^{10}$ molecules/cm$^2$. In some embodiments, the plurality of nucleic acids is a clonal plurality of nucleic acids, for example, as produced by an amplification reaction.

Further is provided technology that finds use in methods for determining the sequence of a nucleic acid. For example, some embodiments provide methods comprising providing a reaction solution comprising the nucleic acid; a polymerase; and an oligonucleotide complementary to the nucleic acid; adding a deoxynucleotide to the reaction solution; and monitoring the pH of the reaction solution, wherein a change in the pH of the reaction solution indicates that the deoxynucleotide was polymerized to the 3' end of the oligonucleotide. One aspect of the technology is that in some embodiments the change in the pH of the reaction solution is greater than or equal to 0.1. Some embodiments provide a method further comprising removing the deoxynucleotide from the reaction solution or inactivating the deoxynucleotide.

In another aspect of the technology, methods are provided for identifying a target base in a single-stranded nucleic acid, the method comprising providing a reaction solution comprising the single-stranded nucleic acid; a polymerase; and an oligonucleotide that hybridizes to the single-stranded nucleic acid at a binding site, wherein the 5' end base of the binding site is directly adjacent to the target base; adding a deoxynucleotide to the reaction solution; and monitoring the pH of the reaction solution with an electrochemical hydrogen ion sensor, wherein a change in the pH of the reaction solution indicates that the deoxynucleotide was polymerized to the 3' end of the oligonucleotide. Detecting a change in the pH of the reaction solution indicates that the nucleotide presently added to the reaction solution has been added to the growing strand, which is complementary to the nucleic acid being sequenced. Thus, in some embodiments a change in the pH of the reaction solution identifies the target base on the strand being sequenced according to a rule selected from the set consisting of: if the deoxynucleotide comprises adenine, the target base is thymine; if the deoxynucleotide comprises guanine, the target base is cytosine; if the deoxynucleotide comprises thymine, the target base is adenine; and if the deoxynucleotide comprises cytosine, the target base is guanine.

In some embodiments the change in the pH of the reaction solution is greater than or equal to 0.1. The electrode used for monitoring pH changes is, in some embodiments, a microfabricated mixed metal oxide electrode and in some embodiments the electrode used for monitoring pH changes is a membrane electrode. In some embodiments, monitoring the pH of the reaction solution comprises comparing a signal from the electrochemical hydrogen ion sensor to a signal from a reference electrode. In some embodiments, the single-stranded nucleic acid covers the electrochemical hydrogen ion sensor at a density of greater than or equal to $2.2 \times 10^{10}$ molecules/cm$^2$. Some embodiments provide that the reaction solution comprises a low ionic strength buffer. Aspects of the technology are embodied in methods and devices. Accordingly, embodiments of the methods provided herein comprise use of the devices described above.

Additional embodiments will be apparent to persons skilled in the relevant art based on the teachings contained herein.

DETAILED DESCRIPTION

The technology provides an electrochemical sensing technology that finds use to measure the associated pH change upon addition of a base in a sequencing by synthesis approach. Per the chemistry of the reaction of base extension, a proton is produced and this leads to a difference in pH that can be measured by an electrochemical analyte sensor. Depending on the nucleotide base made available to the reaction (that includes the polymerase enzyme and appropriate target template), the deduction can be made (based on whether or not a pH change occurs) as to what specific complementary DNA nucleotide base had been added in the process of the extension reaction. For example, if a sample contains a sequence that has an A in it, and a signal is seen when a T is added then it is apparent that an A was present at that particular location. This process can then be applied to deduce in a step by step manner the sequence of a particular segment of nucleic acid by repetitively employing the process and deducing sequence based on pH change as sensed by a pH sensor.

DEFINITIONS

To facilitate an understanding of the present technology, a number of terms and phrases are defined below. Additional definitions are set forth throughout the detailed description.

As used herein, "a" or "an" or "the" can mean one or more than one. For example, "a" cell can mean one cell or a plurality of cells.

As used herein, a "low ionic strength" buffer refers to a solution that comprises a concentration of the buffer sufficient to maintain the buffer at low ionic strength, preferably in a range from about 1 mM to about 100 mM. Suitable buffers for preparation of a low-ionic-strength buffer include, but are not limited to, e.g., glycine, aspartic acid, glutamic acid, sodium succinate, formate, acetate, citrate, phosphate, histidine, and imidazole.

As used herein, the phrase "dNTP" means deoxynucleotidetriphosphate, where the nucleotide is any nucleotide, such as A, T, C, G or U.

As used herein, the phrase "a clonal plurality of nucleic acids" refers to the nucleic acid products that are complete or partial copies of a template nucleic acid from which they were generated. These products are substantially or completely or essentially identical to each other, and they are complementary copies of the template nucleic acid strand from which they are synthesized, assuming that the rate of nucleotide misincorporation during the synthesis of the clonal nucleic acid molecules is 0%.

As used herein, a "nucleic acid" shall mean any nucleic acid molecule, including, without limitation, DNA, RNA and hybrids thereof. The nucleic acid bases that form nucleic acid molecules can be the bases A, C, G, T and U, as well as derivatives thereof. Derivatives of these bases are well known in the art. The term should be understood to include, as equivalents, analogs of either DNA or RNA made from nucleotide analogs. The term as used herein also encompasses cDNA, that is complementary, or copy, DNA produced from an RNA template, for example by the action of reverse transcriptase.

As used herein, a "membrane electrode" is an electrode comprising, for example, a silicon substrate on which is established thin-film structures that make up an electrochemical (e.g., amperometric, potentiometric, conductimetric) transducer, or base sensor. In some embodiments, the base sensor is fabricated on a substantially planar silicon substrate by means of photolithography in combination with the plasma deposition of metallic substances. In some embodiments, succeeding structures are overlaid such as (i) a semipermeable solid film or permselective layer, superimposed over at least a portion of the base sensor, whose function is to promote the adhesion of succeeding layers over the base sensor and most importantly to prevent interfering electroactive species from reaching the catalytic electroactive surface of the base sensor; (ii) a biolayer, superimposed over at least a portion of the permselective layer, in which is incorporated a sufficient amount of a bioactive molecule; and (iii) a layer responsible for attenuating the transport of the analyte species from the sample to the biolayer, thus limiting the amount of analyte which reaches the enzyme to a given fraction of the bulk concentration of analyte in the sample. The base sensor may comprise a unit cell containing two catalytic electrodes of identical geometry and area. This configuration allows a differential type of measurement because on only one of these catalytic electrodes is established a biolayer. Such a differential measurement may, in turn, enable the device to measure a current due to the activity of selected bioactive molecules over and above a background level, especially in circumstances where an interfering species may not be readily excluded by a permselective membrane. In a particular embodiment, a hydrogen ion-sensitive membrane electrode comprises a base layer and a hydrogen ion-sensitive layer produced, for example, as follows: first, combine equal volumes of cyclohexanone and propiophenone. To 1.5 g of this solvent mixture add, with stirring and gently warming, sodium tetraphenylborate (5 mg), tridodecyl amine (75 mg), dibutyl sebacate (620 mg), and 300 mg of high-molecular weight polyvinyl chloride. Also, o-nitrophenyloctylether (620 mg) may be used in place of the dibutyl sebacate. The resulting composition is mixed thoroughly before use and loaded into a microsyringe for to establish the hydrogen ion-sensitive layer in a controllable manner. The microsyringe is preferably equipped with a 25 to 30 gauge needle (EFD Inc.) having an internal diameter of 150 µm and an external diameter of 300 µm. Typically, the microsyringe needle, which includes an elongated member and a needle tip, is made of a metallic material, like stainless steel. Additionally, materials such as synthetic polymers may also be employed in manufacturing the main body of the needle itself. Depending on the pretreatment of the electrode surface and the volume amount of fluid applied, membrane layers of a thickness ranging from about 1 to about 200 µm can be obtained consistently. These and other embodiments of membrane electrodes are described in U.S. Pat. No. 5,200,051, incorporated herein in its entirety for all purposes.

As used herein, a "microfabricated metal oxide electrode" is an ion-sensitive electrode comprising, for example, a conductive metal oxide combined with an insulating material in such a manner that the fundamental bulk conductive properties of the conductive oxide are modified to reduce the redox current that distorts the Nernstian response and therefore the accuracy of the measurement. More particularly, in some embodiments the electrode comprises a Group VIIIB metal oxide and an insulating material having a density of proton binding sites sufficient to provide the sensitivity desired and matrixed in such a way so as to reduce the density of states at the Fermi level of the conductive metal oxide. This combination provides an ion selective electrode having a fast Nernstian ion response and reduced redox interference while maintaining a high level of conductivity at the conductor, long term electro-chemical stability, reduced stabilization time appropriate to equilibrate fresh electrodes, resistance to corrosion and chemical attack, low impedance, and easy adaptation for miniaturization and a variety of electrode configurations.

The electrode material of the present invention may be prepared in a variety of ways known to those skilled in the art. However, the electrodes should be prepared in a manner such that the morphology of the mixture is closely controlled. More particularly, the electrode material should be prepared so that the particle size of the conductive metal oxide in the mixture is reduced enough to minimize redox interference while providing adequate conductivity to permit the electrode to function as a Faradaic electrode. The reduction in particle size of the conductive metal oxide is sufficient that the particles no longer exhibit the bulk properties of the conductive metal oxide, specifically the bulk conductivity. The bulk conductivity property of the conductive metal oxide provides for the rapid electronic exchange which promotes redox reactions. The bulk conductivity property depends on the number of conductive electrons which, in turn, relates to the density of states of the Fermi level. By reducing the particle size, the density states at the Fermi level are reduced and the conductive metal oxide does not exhibit the bulk conductive properties of the material. In the alternative, the electrode material may be prepared by alloying the conductive metal oxide to the insulating material. The amount of redox interference is reduced while maintaining sufficient conductivity to support an electrode in a Faradaic configuration.

The amount of conductivity the material should exhibit is dependent upon the application, preferably upon the impedance of the measurement circuit since the impedance of the material should be less than the impedance of the measuring circuit. For example, if the impedance of the measuring circuit is $10^{12}$ ohms, the impedance of the material is preferably less than about $10^{10}$ ohms. In some embodiments, the insulating material used in the electrode is of the type in which the surface of the material readily exchanges protons. Proton exchange and, in particular, the level of sensitivity in the electrode material to changes in ionic concentration, is related to the density of proton binding sites in the material. The greater the density of proton binding sites the more rapid the proton exchange on the surface of the material and the greater the sensitivity of the material to the ionic concentration. Preferably the density of sites for proton exchange in the insulating material is greater than $10^{13}/cm^2$. The metal oxide electrode may be used in conjunction with catalytic or enzymatic layers to measure an ionic species and calculate the concentration of specific components in the ambient. This may be accomplished by placing at least one layer of material between the metal oxide composition and the ambient to be sensed so as to detect a change of the concentration of ionic species in the layer resulting from exposure of that layer to the ambient. Through the change in the concentration of the ionic species sensed by the metal oxide electrode of the present invention, the concentration can be determined of a species of interest in the ambient. These and other embodiments of microfabricated metal oxide electrodes are described in U.S. Pat. No. 5,009,766, incorporated herein in its entirety for all purposes.

Embodiments of the Technology

The technology relates to using microfabricated mixed metal oxide electrodes (e.g. as provided in U.S. Pat. No. 5,009,766, incorporated herein by reference in its entirety for all purposes) or membrane electrodes (e.g. as provided in U.S. Pat. No. 5,200,051, incorporated herein by reference in its entirety for all purposes) in conjunction with a suitable reference electrode (e.g. as provided in U.S. Pat. No. 4,933,048, incorporated herein by reference in its entirety for all purposes) for sensing and detecting ionic species, e.g. protons, generated from a chemical reaction (e.g., DNA synthesis, DNA polymerization) that can be used to indicate the presence or absence of a molecular target without the use of ion-sensitive field effect transistors or voltage clamped proton detectors. While not limited in the types of electrodes that may be used, it is contemplated that the device comprises microfabricated electrodes suitable for mass production and capable of detecting a wide range of biological molecules (e.g., hydrogen ion). Examples of electrodes are provided in U.S. Pat. Nos. 4,613,422; 4,739,380; 4,933,048; 5,063,081; 5,200,051; 5,837,446; 5,837,454; 6,030,827; 6,379,883; 7,540,948; including reference sensors in U.S. Pat. No. 7,723,099, all of which are incorporated herein by reference in their entireties for all purposes.

One such use is detecting a change in pH as protons are generated or absorbed in different aqueous chemical reactions, more specifically, detecting the proton released when a dNTP base is incorporated in a DNA template by a polymerase enzyme. In this reaction, DNA polymerase incorporates a complementary dNTP base into a growing chain of DNA, with concurrent release of pyrophosphate ($PP_i$) and a single proton. If enough protons are released in the vicinity of the metal oxide electrode surface, a measurable pH change can be detected by the electrode, thereby indicating successful integration of a base in the growing complementary strand. Transduction of the hydrogen ion concentration into a signal is by an electrochemical (e.g., amperometric, potentiometric (voltammetric), or conductimetric) means. Potentiometric and amperometric techniques are preferred because the output signal may most easily be related directly to the response of the electrode to a particular analyte.

Since most enzymatic reactions benefit from buffered conditions for proper enzymatic function, it is natural for the present invention to use low ionic strength buffers to carry out pH measurements. High concentration buffer solutions would have the undesirable effect of suppressing pH changes, thereby negating the usefulness of the ion selective sensing electrode. For example, in some embodiments a buffer (e.g., a Tris buffer) is used at 100 mM, at 10 mM, or at 1 mM. In some embodiments, the reaction solution comprises no buffer or has no added buffer (e.g., any buffer present is residual and is carried over from other components added to the reaction such as the enzyme, salts, and/or dNTPs). In some embodiments the reaction solution comprises salts (at exemplary concentrations) such as 0.5 M NaCl, 100 mM $MgCl_2$, 10 mM dithiothreitol (DTT).

Various pH electrodes have been employed as clinical chemistry-based biosensors. As such, it has been demonstrated that an ion-specific metal oxide electrode, when used in parallel with a corresponding reference electrode, can detect pH changes as small as 0.1 pH unit. For example, a small (200 µm diameter) metal oxide electrode surrounded by a wall 30 µm high could be used as a reaction container to monitor release of protons from a clonal population of target DNA molecules. Target molecules may either be coated on the electrode surface or attached to microparticle beads that are placed inside each electrode well compartment. It is assumed that the sequencing device would have a large array of such electrodes.

As sequencing reagents are introduced into the device, a single proton would be released for each target molecule in the compartment. Depending on the surface density of bound DNA target molecules, a change in localized pH would result in the electrode compartment if a specific dNTP base was added to the target.

An example calculation of possible pH changes within the electrode compartment is shown below. It assumes the sequencing buffer used in the assay is a low concentration buffer with a pH of 8. A change of at least 0.1 pH unit would be detected by the electrode. The magnitude of the actual pH change would be proportional to the number of bound target molecules present in the compartment.

| electrode diameter, µm | electrode wall height, µm | target molecule loading, molecules/$cm^2$ | localized pH | pH unit difference from pH 8.0 |
|---|---|---|---|---|
| 200 | 30 | 6.70E+11 | 6.4 | 1.6 |
| 200 | 30 | 3.00E+11 | 6.8 | 1.2 |
| 200 | 30 | 1.00E+11 | 7.3 | 0.7 |
| 200 | 30 | 5.00E+10 | 7.6 | 0.4 |
| 200 | 30 | 3.00E+10 | 7.8 | 0.2 |
| 200 | 30 | 2.20E+10 | 7.9 | 0.1 |

It is assumed that control measures should be in place to control the rate of proton diffusion away from the electrode surface into the surrounding solution. Such measures include, but are not limited to, adding support micro particles in the electrode compartment or placing a physical barrier over the top of the compartment. Both methods work by restricting the movement of highly diffusible protons after addition of the dNTP base, allowing for a longer response time for measuring the localized proton concentration.

The technology contemplates the use of a pH electrode to monitor the sequencing of nucleic acids using any extant or future sequencing technology and/or chemistry and/or reaction scheme appropriate for the technology herein described.

Accordingly, in some embodiments, any suitable systems, devices, compositions, and methods for nucleic acid sequence analysis are within the scope of the present invention. Illustrative non-limiting examples of nucleic acid sequencing techniques include, but are not limited to, "next generation" sequencing techniques. While various of these approaches employ different detection mechanisms, various aspects of their sample preparation, sequencing reactions, and/or data analysis may be employed in the approaches described herein.

In some embodiments, DNA sequencing methodologies provided by the present invention comprise Second Generation (a.k.a. Next Generation or Next-Gen), Third Generation (a.k.a. Next-Next-Gen), or Fourth Generation (a.k.a. N3-Gen) sequencing technologies including, but not limited to, pyrosequencing, sequencing-by-ligation, single molecule sequencing, sequence-by-synthesis (SBS), massive parallel clonal, massive parallel single molecule SBS, massive parallel single molecule real-time, massive parallel single molecule real-time nanopore technology, etc. Morozova and Marra provide a review of some such technologies in Genomics, 92: 255 (2008), herein incorporated by reference in its entirety. Those of ordinary skill in the art will recognize that because RNA is less stable in the cell and more prone to nuclease attack experimentally RNA is usually reverse transcribed to DNA before sequencing.

A number of DNA sequencing techniques are known in the art, including fluorescence-based sequencing methodologies (See, e.g., Birren et al., Genome Analysis: Analyzing DNA, 1, Cold Spring Harbor, N.Y.; herein incorporated by reference in its entirety). In some embodiments, automated sequencing techniques understood in that art are utilized. In some embodiments, the present invention provides parallel sequencing of partitioned amplicons (PCT Publication No.: WO2006084132 to Kevin McKernan et al., herein incorporated by reference in its entirety). In some embodiments, DNA sequencing is achieved by parallel oligonucleotide extension (See, e.g., U.S. Pat. No. 5,750,341 to Macevicz et al., and U.S. Pat. No. 6,306,597 to Macevicz et al., both of which are herein incorporated by reference in their entireties). Additional examples of sequencing techniques include the Church polony technology (Mitra et al., 2003, Analytical Biochemistry 320, 55-65; Shendure et al., 2005 Science 309, 1728-1732; U.S. Pat. No. 6,432,360, U.S. Pat. No. 6,485,944, U.S. Pat. No. 6,511,803; herein incorporated by reference in their entireties), the 454 picotiter pyrosequencing technology (Margulies et al., 2005 Nature 437, 376-380; US 20050130173; herein incorporated by reference in their entireties), the Solexa single base addition technology (Bennett et al., 2005, Pharmacogenomics, 6, 373-382; U.S. Pat. No. 6,787,308; U.S. Pat. No. 6,833,246; herein incorporated by reference in their entireties), the Lynx massively parallel signature sequencing technology (Brenner et al. (2000). Nat. Biotechnol. 18:630-634; U.S. Pat. No. 5,695,934; U.S. Pat. No. 5,714,330; herein incorporated by reference in their entireties), and the Adessi PCR colony technology (Adessi et al. (2000). Nucleic Acid Res. 28, E87; WO 00018957; herein incorporated by reference in its entirety).

Next-generation sequencing (NGS) methods share the common feature of massively parallel, high-throughput strategies, with the goal of lower costs in comparison to older sequencing methods (see, e.g., Voelkerding et al., Clinical Chem., 55: 641-658, 2009; MacLean et al., Nature Rev. Microbiol., 7: 287-296; each herein incorporated by reference in their entirety). NGS methods can be broadly divided into those that typically use template amplification and those that do not. Amplification-requiring methods include pyrosequencing commercialized by Roche as the 454 technology platforms (e.g., GS 20 and GS FLX), the Solexa platform commercialized by Illumina, and the Supported Oligonucleotide Ligation and Detection (SOLiD) platform commercialized by Applied Biosystems. Non-amplification approaches, also known as single-molecule sequencing, are exemplified by the HeliScope platform commercialized by Helicos BioSciences, and emerging platforms commercialized by VisiGen, Oxford Nanopore Technologies Ltd., Life Technologies/Ion Torrent, and Pacific Biosciences, respectively.

In pyrosequencing (Voelkerding et al., *Clinical Chem.*, 55: 641-658, 2009; MacLean et al., *Nature Rev. Microbiol.*, 7: 287-296; U.S. Pat. No. 6,210,891; U.S. Pat. No. 6,258,568; each herein incorporated by reference in its entirety), template DNA is fragmented, end-repaired, ligated to adaptors, and clonally amplified in-situ by capturing single template molecules with beads bearing oligonucleotides complementary to the adaptors. Each bead bearing a single template type is compartmentalized into a water-in-oil microvesicle, and the template is clonally amplified using a technique referred to as emulsion PCR. The emulsion is disrupted after amplification and beads are deposited into individual wells of a picotitre plate functioning as a flow cell during the sequencing reactions. Ordered, iterative introduction of each of the four dNTP reagents occurs in the flow cell in the presence of sequencing enzymes and luminescent reporter such as luciferase. In the event that an appropriate dNTP is added to the 3' end of the sequencing primer, the resulting production of ATP causes a burst of luminescence within the well, which is recorded using a CCD camera. It is possible to achieve read lengths greater than or equal to 400 bases, and $10^6$ sequence reads can be achieved, resulting in up to 500 million base pairs (Mb) of sequence.

In the Solexa/Illumina platform (Voelkerding et al., *Clinical Chem.*, 55: 641-658, 2009; MacLean et al., *Nature Rev. Microbiol.*, 7: 287-296; U.S. Pat. No. 6,833,246; U.S. Pat. No. 7,115,400; U.S. Pat. No. 6,969,488; each herein incorporated by reference in its entirety), sequencing data are produced in the form of shorter-length reads. In this method, single-stranded fragmented DNA is end-repaired to generate 5'-phosphorylated blunt ends, followed by Klenow-mediated addition of a single A base to the 3' end of the fragments. A-addition facilitates addition of T-overhang adaptor oligonucleotides, which are subsequently used to capture the template-adaptor molecules on the surface of a flow cell that is studded with oligonucleotide anchors. The anchor is used as a PCR primer, but because of the length of the template and its proximity to other nearby anchor oligonucleotides, extension by PCR results in the "arching over" of the molecule to hybridize with an adjacent anchor oligonucleotide to form a bridge structure on the surface of the flow cell. These loops of DNA are denatured and cleaved. Forward strands are then sequenced with reversible dye terminators. The sequence of incorporated nucleotides is determined by detection of post-incorporation fluorescence, with each fluor and block removed prior to the next cycle of dNTP addition. Sequence read length ranges from 36 nucleotides to over 50 nucleotides, with overall output exceeding 1 billion nucleotide pairs per analytical run.

Sequencing nucleic acid molecules using SOLiD technology (Voelkerding et al., *Clinical Chem.*, 55: 641-658, 2009; MacLean et al., *Nature Rev. Microbiol.*, 7: 287-296; U.S. Pat. No. 5,912,148; U.S. Pat. No. 6,130,073; each herein incorporated by reference in their entirety) also involves fragmentation of the template, ligation to oligonucleotide adaptors, attachment to beads, and clonal amplification by emulsion PCR. Following this, beads bearing template are immobilized on a derivatized surface of a glass flow-cell, and a primer complementary to the adaptor oligonucleotide is annealed. However, rather than utilizing this primer for 3' extension, it is instead used to provide a 5' phosphate group for ligation to interrogation probes containing two probe-specific bases followed by 6 degenerate bases and one of four fluorescent labels. In the SOLiD system, interrogation probes have 16 possible combinations of the two bases at the 3' end of each probe, and one of four fluors at the 5' end. Fluor color, and thus identity of each probe, corresponds to specified color-space coding schemes. Multiple rounds (usually 7) of probe annealing, ligation, and fluor detection are followed by denaturation, and then a second round of sequencing using a primer that is offset by one base relative to the initial primer. In this manner, the template sequence can be computationally re-constructed, and template bases are interrogated twice, resulting in increased accuracy. Sequence read length averages 35 nucleotides, and overall output exceeds 4 billion bases per sequencing run.

In certain embodiments, nanopore sequencing is employed (see, e.g., Astier et al., J. Am. Chem. Soc. 2006 Feb. 8; 128(5):1705-10, herein incorporated by reference). The theory behind nanopore sequencing has to do with what occurs when a nanopore is immersed in a conducting fluid and a potential (voltage) is applied across it. Under these conditions a slight electric current due to conduction of ions through the nanopore can be observed, and the amount of current is exceedingly sensitive to the size of the nanopore. As each base of a nucleic acid passes through the nanopore, this causes a change in the magnitude of the current through the nanopore that is distinct for each of the four bases, thereby allowing the sequence of the DNA molecule to be determined.

In certain embodiments, HeliScope by Helicos BioSciences is employed (Voelkerding et al., *Clinical Chem.*, 55: 641-658, 2009; MacLean et al., *Nature Rev. Microbiol.*, 7: 287-296; U.S. Pat. No. 7,169,560; U.S. Pat. No. 7,282,337; U.S. Pat. No. 7,482,120; U.S. Pat. No. 7,501,245; U.S. Pat. No. 6,818,395; U.S. Pat. No. 6,911,345; U.S. Pat. No. 7,501,245; each herein incorporated by reference in their entirety). Template DNA is fragmented and polyadenylated at the 3' end, with the final adenosine bearing a fluorescent label. Denatured polyadenylated template fragments are ligated to poly(dT) oligonucleotides on the surface of a flow cell. Initial physical locations of captured template molecules are recorded by a CCD camera, and then label is cleaved and washed away. Sequencing is achieved by addition of polymerase and serial addition of fluorescently-labeled dNTP reagents. Incorporation events result in fluor signal corresponding to the dNTP, and signal is captured by a CCD camera before each round of dNTP addition. Sequence read length ranges from 25-50 nucleotides, with overall output exceeding 1 billion nucleotide pairs per analytical run.

The Ion Torrent technology is a method of DNA sequencing based on the detection of hydrogen ions that are released during the polymerization of DNA (see, e.g., *Science* 327 (5970): 1190 (2010); U.S. Pat. Appl. Pub. Nos. 20090026082, 20090127589, 20100301398, 20100197507, 20100188073, and 20100137143, incorporated by reference in their entireties for all purposes). A microwell contains a template DNA strand to be sequenced. Beneath the layer of microwells is a hypersensitive ISFET ion sensor. All layers are contained within a CMOS semiconductor chip, similar to that used in the electronics industry. When a dNTP is incorporated into the growing complementary strand a hydrogen ion is released, which triggers a hypersensitive ion sensor. If homopolymer repeats are present in the template sequence, multiple dNTP molecules will be incorporated in a single cycle. This leads to a corresponding number of released hydrogens and a proportionally higher electronic signal. This technology differs from other sequencing technologies in that no modified nucleotides or optics are used. The per base accuracy of the Ion Torrent sequencer is ~99.6% for 50 base reads, with ~100 Mb generated per run. The read-length is 100 base pairs. The accuracy for homopolymer repeats of 5 repeats in length is ~98%. The benefits of ion semiconductor sequencing are rapid sequencing speed and low upfront and operating costs. However, the cost of acquiring a pH-mediated sequencer is approximately $50,000, excluding sample preparation equipment and a server for data analysis.

Another exemplary nucleic acid sequencing approach that may be adapted for use with the present invention was developed by Stratos Genomics, Inc. and involves the use of Xpandomers. This sequencing process typically includes providing a daughter strand produced by a template-directed synthesis. The daughter strand generally includes a plurality of subunits coupled in a sequence corresponding to a contiguous nucleotide sequence of all or a portion of a target nucleic acid in which the individual subunits comprise a tether, at least one probe or nucleobase residue, and at least one selectively cleavable bond. The selectively cleavable bond(s) is/are cleaved to yield an Xpandomer of a length longer than the plurality of the subunits of the daughter strand. The Xpandomer typically includes the tethers and reporter elements for parsing genetic information in a sequence corresponding to the contiguous nucleotide sequence of all or a portion of the target nucleic acid. Reporter elements of the Xpandomer are then detected. Additional details relating to Xpandomer-based approaches are described in, for example, U.S. Pat. Pub No. 20090035777, entitled "HIGH THROUGHPUT NUCLEIC ACID SEQUENCING BY EXPANSION," filed Jun. 19, 2008, which is incorporated herein in its entirety.

Other emerging single molecule sequencing methods include real-time sequencing by synthesis using a VisiGen platform (Voelkerding et al., *Clinical Chem.*, 55: 641-58, 2009; U.S. Pat. No. 7,329,492; U.S. patent application Ser. No. 11/671,956; U.S. patent application Ser. No. 11/781,166; each herein incorporated by reference in their entirety) in which immobilized, primed DNA template is subjected to strand extension using a fluorescently-modified polymerase and florescent acceptor molecules, resulting in detectible fluorescence resonance energy transfer (FRET) upon nucleotide addition.

Another real-time single molecule sequencing system developed by Pacific Biosciences (Voelkerding et al., *Clinical Chem.*, 55: 641-658, 2009; MacLean et al., *Nature Rev. Microbiol.*, 7: 287-296; U.S. Pat. No. 7,170,050; U.S. Pat. No. 7,302,146; U.S. Pat. No. 7,313,308; U.S. Pat. No. 7,476,503; all of which are herein incorporated by reference) utilizes reaction wells 50-100 nm in diameter and encompassing a reaction volume of approximately 20 zeptoliters ($10^{-21}$ L). Sequencing reactions are performed using immobilized template, modified phi29 DNA polymerase, and high local concentrations of fluorescently labeled dNTPs. High local concentrations and continuous reaction conditions allow incorporation events to be captured in real time by fluor signal detection using laser excitation, an optical waveguide, and a CCD camera.

In certain embodiments, the single molecule real time (SMRT) DNA sequencing methods using zero-mode waveguides (ZMWs) developed by Pacific Biosciences, or similar methods, are employed. With this technology, DNA sequencing is performed on SMRT chips, each containing thousands of zero-mode waveguides (ZMWs). A ZMW is a hole, tens of nanometers in diameter, fabricated in a 100 nm metal film deposited on a silicon dioxide substrate. Each ZMW becomes a nanophotonic visualization chamber providing a detection volume of just 20 zeptoliters ($10^{-21}$ L). At this volume, the activity of a single molecule can be detected amongst a background of thousands of labeled nucleotides. The ZMW provides a window for watching DNA polymerase as it performs sequencing by synthesis. Within each chamber, a single DNA polymerase molecule is attached to the bottom surface such that it permanently resides within the detection volume. Phospholinked nucleotides, each type labeled with a different colored fluorophore, are then introduced into the reaction solution at high concentrations which promote enzyme speed, accuracy, and processivity. Due to the small size of the ZMW, even at these high, biologically relevant concentrations, the detection volume is occupied by nucleotides only a small fraction of the time. In addition, visits to the detection volume are fast, lasting only a few microseconds, due to the very small distance that diffusion has to carry the nucleotides. The result is a very low background.

Processes and systems for such real time sequencing that may be adapted for use with the invention are described in, for example, U.S. Pat. No. 7,405,281, entitled "Fluorescent nucleotide analogs and uses therefor", issued Jul. 29, 2008 to Xu et al.; U.S. Pat. No. 7,315,019, entitled "Arrays of optical confinements and uses thereof", issued Jan. 1, 2008 to Turner et al.; U.S. Pat. No. 7,313,308, entitled "Optical analysis of molecules", issued Dec. 25, 2007 to Turner et al.; U.S. Pat. No. 7,302,146, entitled "Apparatus and method for analysis of molecules", issued Nov. 27, 2007 to Turner et al.; and U.S. Pat. No. 7,170,050, entitled "Apparatus and methods for optical analysis of molecules", issued Jan. 30, 2007 to Turner et al.; and U.S. Pat. Pub. Nos. 20080212960, entitled "Methods and systems for simultaneous real-time monitoring of optical signals from multiple sources", filed Oct. 26, 2007 by Lundquist et al.; 20080206764, entitled "Flowcell system for single molecule detection", filed Oct. 26, 2007 by Williams et al.; 20080199932, entitled "Active surface coupled polymerases", filed Oct. 26, 2007 by Hanzel et al.; 20080199874, entitled "CONTROLLABLE STRAND SCISSION OF MINI CIRCLE DNA", filed Feb. 11, 2008 by Otto et al.; 20080176769, entitled "Articles having localized molecules disposed thereon and methods of producing same", filed Oct. 26, 2007 by Rank et al.; 20080176316, entitled "Mitigation of photodamage in analytical reactions", filed Oct. 31, 2007 by Eid et al.; 20080176241, entitled "Mitigation of photodamage in analytical reactions", filed Oct. 31, 2007 by Eid et al.; 20080165346, entitled "Methods and systems for simultaneous real-time monitoring of optical signals from multiple sources", filed Oct. 26, 2007 by Lundquist et al.; 20080160531, entitled "Uniform surfaces for hybrid material substrates and methods for making and using same", filed Oct. 31, 2007 by Korlach; 20080157005, entitled "Methods and systems for simultaneous real-time monitoring of optical signals from multiple sources", filed Oct. 26, 2007 by Lundquist et al.; 20080153100, entitled "Articles having localized molecules disposed thereon and methods of producing same", filed Oct. 31, 2007 by Rank et al.; 20080153095, entitled "CHARGE SWITCH NUCLEOTIDES", filed Oct. 26, 2007 by Williams et al.; 20080152281, entitled "Substrates, systems and methods for analyzing materials", filed Oct. 31, 2007 by Lundquist et al.; 20080152280, entitled "Substrates, systems and methods for analyzing materials", filed Oct. 31, 2007 by Lundquist et al.; 20080145278, entitled "Uniform surfaces for hybrid material substrates and methods for making and using same", filed Oct. 31, 2007 by Korlach; 20080128627, entitled "SUBSTRATES, SYSTEMS AND METHODS FOR ANALYZING MATERIALS", filed Aug. 31, 2007 by Lundquist et al.; 20080108082, entitled "Polymerase enzymes and reagents for enhanced nucleic acid sequencing", filed Oct. 22, 2007 by Rank et al.; 20080095488, entitled "SUBSTRATES FOR PERFORMING ANALYTICAL REACTIONS", filed Jun. 11, 2007 by Foquet et al.; 20080080059, entitled "MODULAR OPTICAL COMPONENTS AND SYSTEMS INCORPORATING SAME", filed Sep. 27, 2007 by Dixon et al.; 20080050747, entitled "Articles having localized molecules disposed thereon and methods of producing and using same", filed Aug. 14, 2007 by Korlach et al.; 20080032301, entitled "Articles having localized molecules disposed thereon and methods of producing same", filed Mar. 29, 2007 by Rank et al.; 20080030628, entitled "Methods and systems for simultaneous real-time monitoring of optical signals from multiple sources", filed Feb. 9, 2007 by Lundquist et al.; 20080009007, entitled "CONTROLLED INITIATION OF PRIMER EXTENSION", filed Jun. 15, 2007 by Lyle et al.; 20070238679, entitled "Articles having localized molecules disposed thereon and methods of producing same", filed Mar. 30, 2006 by Rank et al.; 20070231804, entitled "Methods, systems and compositions for monitoring enzyme activity and applications thereof", filed Mar. 31, 2006 by Korlach et al.; 20070206187, entitled "Methods and systems for simultaneous real-time monitoring of optical signals from multiple sources", filed Feb. 9, 2007 by Lundquist et al.; 20070196846, entitled "Polymerases for nucleotide analogue incorporation", filed Dec. 21, 2006 by Hanzel et al.; 20070188750, entitled "Methods and systems for simultaneous real-time monitoring of optical signals from multiple sources", filed Jul. 7, 2006 by Lundquist et al.; 20070161017, entitled "MITIGATION OF PHOTODAMAGE IN ANALYTICAL REACTIONS", filed Dec. 1, 2006 by Eid et al.; 20070141598, entitled "Nucleotide Compositions and Uses Thereof", filed Nov. 3, 2006 by Turner et al.; 20070134128, entitled "Uniform surfaces for hybrid material substrate and methods for making and using same", filed Nov. 27, 2006 by Korlach; 20070128133, entitled "Mitigation of photodamage in analytical reactions", filed Dec. 2, 2005 by Eid et al.; 20070077564, entitled "Reactive surfaces, substrates and methods of producing same", filed Sep. 30, 2005 by Roitman et al.; 20070072196, entitled "Fluorescent nucleotide analogs and uses therefore", filed Sep. 29, 2005 by Xu et al; and 20070036511, entitled "Methods and systems for monitoring multiple optical signals from a single source", filed Aug. 11, 2005 by Lundquist et al.; and Korlach et al. (2008) "Selective aluminum passivation for targeted immobilization of single DNA polymerase molecules in zero-mode waveguide nanostructures" PNAS 105(4): 1176-81, all of which are herein incorporated by reference in their entireties.

In some embodiments, the pH electrode(s) is/are incorporated into a cartridge, e.g., a disposable cartridge for performing the sequencing methods described herein. The cartridge's longest dimension is on the order of approximately 1-10 cm (e.g., 1, 5, 10 cm, e.g., approximately the size of a deck of playing cards or smaller), although larger and smaller dimensions may be employed.

The cartridge comprises one or more pH electrodes and, in some embodiments, one or more reference electrodes, one or more chambers for holding fluids or other sample types. In some embodiments the cartridge comprises a multiplexer for processing signals received from the electrodes and sending data signals to an output, and in some embodiments, to a reading apparatus. In some embodiments the cartridge comprises a demultiplexer receiving signals from the reading apparatus and routing signals to the electrodes. The cartridge further comprises fluid handling components (e.g., inlet ports, outlet ports, metering means to measure and provide specific volumes of fluids, and conduits for handling and transporting the sample and other fluids) and the necessary electronic connections for sending and receiving electronic signals among the multiplexer, demultiplexer, the reading apparatus, and the electrodes. See, for example, U.S. Pat. Appl. Ser. No. 61/481,592, incorporated herein by reference in its entirety for all purposes.

The cartridge is adapted for insertion into a reading apparatus (e.g., a hand-held device such as the Abbott Point of Care i-STAT Portable Handheld) and accordingly has a plurality of mechanical and electrical connections for physically and electrically interfacing with the reading apparatus. The reading apparatus is a hand-held device having dimensions of approximately 5-10 cm×5-10 cm×20-30 cm and weighs approximately kilogram or less. Furthermore, in some embodiments the cartridge comprises one or more chambers in which is stored a fluid for, e.g., washing the electrodes, providing one or more nucleotides, providing a solution to remove and/or inactivate one or more nucleotides, providing a polymerase, or providing some other fluid (e.g., a buffer, an amending solution, or some other solution) that is appropriate for the sequencing.

Embodiments of the cartridges take many forms and configurations and they are constructed from many suitable materials. Cartridges having similar sizes and form factors are provided, for example, in U.S. Pat. No. 7,419,821, incorporated herein in its entirety for all purposes. Furthermore, other similar cartridges include a disposable sensing device for measuring analytes in a blood sample as disclosed in U.S. Pat. Nos. 5,096,669; 6,750,053; 7,723,099. Other devices are disclosed in U.S. Pat. Nos. 5,628,961 and 5,447,440 for measuring clotting time. These devices employ a reading apparatus and a cartridge that fits into the reading apparatus for the purpose of measuring analyte concentrations and viscosity changes in a blood sample as a function of time.

In some embodiments, the cartridges are used with a single sample. The use of such cartridges provides a convenient way to test (e.g., sequence) samples (e.g., a nucleic acid) while minimizing sample contamination and sample carry-over risks. Appropriately, in some embodiments, the cartridges are disposable.

Furthermore, embodiments of the technology provided herein comprise a reading apparatus (e.g., a hand-held) that is configured to accept a sequencing cartridge (and, accordingly, the technology provides a sequencing cartridge configured to be inserted into and interface with the reading apparatus). The reading apparatus is configured to send and receive signals to and from the cartridge. For example, these signals control the pH electrodes and process data received from the pH electrodes. In some embodiments the reading apparatus comprises a demultiplexer for decoding a signal sent by the cartridge. Such a demultiplexer can be provided by software, firmware, by a dedicated integrated circuit, or a combination thereof. Software and firmware updates for providing demultiplexer capabilities can be performed on reading apparatuses currently being used by the installed user base.

Some embodiments of the technology provided herein further comprise functionalities for collecting, storing, and/or analyzing data (e.g., nucleotide sequence data). For example, in some embodiments the reading apparatus comprises a processor, a memory, and/or a database for, e.g., storing and executing instructions, analyzing data, performing calculations using the data, transforming the data, and storing the data. In some embodiments, the reading apparatus is configured to calculate a function of data received from the cartridge. In some embodiments the reading apparatus comprises software configured for medical or clinical results reporting and in some embodiments the apparatus comprises software to support non-clinical results reporting.

Many diagnostics involve determining the presence of or nucleotide sequence of one or more nucleic acids, and an equation comprising variables representing the presence or sequence properties of multiple nucleic acids produces a value that finds use in making a diagnosis or assessing the presence or qualities of a nucleic acid. As such, in some embodiments the reading apparatus calculates this value and, in some embodiments, presents the value to the user of the device, uses the value to produce an indicator related to the result (e.g., an LED, an icon on an LCD, a sound, or the like), stores the value, transmits the value, or uses the value for additional calculations.

Moreover, in some embodiments a processor is configured to control the reading apparatus. In some embodiments, the processor is used to initiate and/or terminate the measurement and data collection relating to a sequencing reaction. In some embodiments, the device comprises a user interface (e.g., a keyboard, buttons, dials, switches, and the like) for receiving user input that is used by the processor to direct a measurement. In some embodiments, the device further comprises a data output for transmitting (e.g., by a wired or wireless connection) data to an external destination, e.g., a computer, a display, a network, and/or an external storage medium. Some embodiments provide that the device is a small, handheld, portable device incorporating these features and components. Examples of a reading apparatus are provided in U.S. Pat. Nos. 5,096,669 and 5,821,399, which are both hereby incorporated by reference in their respective entireties for all purposes.

The device finds use in assaying the presence of one or more nucleic acids and/or providing the sequence of one or more nucleic acids. Accordingly, the technology provided herein finds use in the medical, clinical, and emergency medical fields. In some embodiments the device is used to assay biological samples. In such an assay, the biological sample comprises a nucleic acid and sequencing the nucleic acid is indicative of a state or a property of the sample and, in some embodiments, the subject from which the sample was taken. Some relevant samples include, but are not limited to, whole blood, lymph, plasma, serum, saliva, urine, stool, perspiration, mucus, tears, cerebrospinal fluid, nasal secretion, cervical or vaginal secretion, semen, pleural fluid, amniotic fluid, peritoneal fluid, middle ear fluid, joint fluid, gastric aspirate, a tissue homogenate, a cell homogenate, or the like.

Furthermore, in some embodiments the sample comprises or is suspected to comprise a composition associated with bioterrorism, e.g., a biological agent. A biological agent is, or is derived from, a living, typically pathogenic, biological organism (e.g., a bacterium, a virus, a eukaryote such as a fungus or a parasite). In some embodiments the sample comprises a biological toxin or other substance derived from a biological source (e.g., a small molecule, a protein, a prion). Bioterrorism agents are, or are derived from, biological sources; thus, particular nucleic acid signature sequences can be used to detect or identify the biological agent. For example, the device can be used to detect a PCR amplicon, a virulence factor gene, or genes encoding the production of a toxin, and/or markers associated with drug resistance.

Biological agents, some of military importance include, but are not limited to, *Bacillus anthracis* (causative agent of anthrax); *Staphylococcus* spp.; *Brucella abortus, Brucella melitensis*, and *Brucella suis* (causative agents of brucellosis); *Vibrio cholerae* (causative agent of cholera); *Corynebacterium diphtheriae* (causative agent of diphtheria); *Cryptosporidium parvum; Shigella dysenteriae* and *Escherichia coli* (causative agents of dysentery); *Burkholderia mallei* (causative agent of glanders); *Listeria monocytogenes* (causative agent of listerosis); *Burkholderia* pseudomallei (causative agent of meliodosis); *Yersinia pestis* (causative agent of plague); *Francisella* tularensis (causative agent of tularemia); *Chlamydia psittaci* (causative agent of psittacosis); *Coxiella* burtetii (causative agent of Q fever); Ricketsia rickettsii (causative agent of Rocky Mountain spotted fever); *Rickettsia prowazekii* and *Rickettsia* typhi (causative agents of typhus); *Coccidioides immitis* (causative agent of coccidiomycosis); Eastern, Western, and Venezuelan equine encephalitis viruses (causative agents of Equine encephalitis); Japanese encephalitis virus (causative agent of Japanese encephalitis); Rift Valley Fever virus (causative agent of Rift Valley fever); Variola virus (causative agent of smallpox); Yellow fever virus (causative agent of yellow fever); arenavirus (causative agent of Lassa fever and the Argentine, Bolivian, Brazilian, and Venezuelan hemorrhagic fevers); other viruses causative of hemorrhagic fevers; other viruses causative of viral encephalitis; Marburg virus; Ebola virus; Nipad virus; hantavirus; SARS; H1N1 influenza virus.

Along with smallpox, anthrax, plague, botulism, and tularemia, hemorrhagic fever viruses are among the six agents identified by the Centers for Disease Control and Prevention (CDC) as the most likely to be used as biological weapons. Hemorrhagic fever viruses include, but are not limited to, the arenaviridae (e.g., Lujo virus); the bunyaviridae (e.g., hantavirus); nairovirus (e.g., the Crimean-Congo hemorrhagic fever virus); Phlebovirus genus (Rift Valley fever virus); filoviridae (e.g., Ebola and Marburg viruses); and flaviviridae (e.g., dengue, yellow fever, Omsk hemorrhagic fever virus, and Kyasanur Forest disease virus).

While the technology finds use in detecting these and other agents in the context of bioterrorism, the technology is also used to detect the same and/or other agents in other contexts and applications. For example, the technology is useful to analyze samples from diseased patients or other subjects suspected of having a disease or having been exposed to a disease.

Although the disclosure herein refers to certain illustrated embodiments, it is to be understood that these embodiments are presented by way of example and not by way of limitation. These embodiments are further understood by the following examples.

EXAMPLES

Example 1

During the development of embodiments of the technology provided herein, it was demonstrated that DNA synthesis produces measurable pH changes.

Oligonucleotides and Enzymes

Synthetic oligonucleotides (Integrated DNA Technologies, Coralville, Iowa) were designed and synthesized to simulate the first steps of DNA synthesis (see Table 1).

TABLE 1 oligonucleotide sequences

| name | SEQ ID NO | oligonucletide sequence (5' to 3') |
|---|---|---|
| isX001 | 1 | 5AmMC6-TTTTTTTTTTTTTTTTTTTT AGTTATGCAACGCGGGAGTTGTGTATGAAGT |
| isX003 | 2 | TGCATGCAACTTCATACACAACTCCCGCGTT GCATAACT |
| isX006 | 3 | GCATGCATACTTCATACACAACTCCCGCGTT GCATAACT | isX001 serves as the primer for DNA synthesis using either isX003 or isX006 as the template for DNA synthesis. The underlined sequence in isX003 and isX006 is the same and is complementary to the underlined sequence in isX001. The non-underlined portions of isX003 and isX006 are the regions that are synthesized by the reaction. The free 3'-hydroxyl group of isX001 permits extension with the appropriate complementary DNA sequence. The T-tail with an amino group (designated by 5AmMC6) was selected as a potential linkage group. The oligonucleotides are designed such that upon annealing of isX003 to isX001, the first base to be added to the 3' end of isX001 is a T as directed by the A in the isX003 template; likewise, upon annealing of isX006 to isX001, the first base to be added to the 3' end of isX001 is an A as directed by the T in the isX006 template.

Klenow Exo DNA polymerase (New England Biolabs, Ipswitch, Mass.) was used for DNA synthesis. This enzyme lacks both 5'→3' and 3'→5' exonuclease activity and thus does not cleave the bonds of linked bases in DNA.

Buffers

The use of a conventional buffered reaction solution hindered initial attempts to monitor a pH change associated with DNA synthesis. To address this issue, experiments were performed to determine if reaction solutions comprising low concentrations of Tris buffer would solve the problems presented by conventional buffers. Three new 10× buffer solutions were prepared comprising 0.5 M NaCl, 100 mM $MgCl_2$, 10 mM DTT, and Tris at 100 mM, 10 mM, or 1 mM. These solutions are designated DSB-A, DSB-B, and DSB-C, respectively. The composition of DSB-A is equivalent to the commercial buffer NEBuffer 2 (New England Biolabs), which thus served as a control.

The buffers were first tested to assess buffer conditions suitable for the DNA synthesis reaction. To test the buffers, test reactions comprising a final concentration of 1×DSB-A, DSB-B, or DSB-C buffer (a final Tris concentration of 10 mM, 1 mM, or 0.1 mM), 100 pmol of isX001, 100 pmol of isX006, 0.05 mM dATP, $3.3 \times 10^{-9}$ mmol alpha-$^{32}$P-dATP (0.74 MBq), and 10 units of DNA polymerase in 20 µl were incubated at 37° C. for 1 hour. The reactions were loaded onto a 20% acrylamide gel comprising 7 M urea and electrophoresed for approximately 1 hour and then autoradiographed. The results showed that the DNA synthesis reaction yields similar amounts of product in the reaction solution comprising Tris buffer at 10 mM, 1 mM, and 0.1 mM.

Measurement of pH Changes Associated with DNA Synthesis

After development of buffers suitable for DNA synthesis, experiments were performed to test if the buffers were appropriate for detecting pH changes associated with DNA synthesis. It was first determined that measuring pH changes in these buffers during an extension reaction were problematic. Accordingly, the Tris concentration was reduced further by preparing and using an additional 10× reaction solution (DSB-D) comprising 0.5 M NaCl, 100 mM $MgCl_2$, and 10 mM DTT, but that did not comprise Tris buffer.

A test reaction similar to that described above was prepared. The reaction comprised a final concentration of 1×DSB-A, DSB-B, DSB-C, or DSB-D (a final Tris concentration of 10 mM, 1 mM, or 0.1 mM, or lacking Tris), 100 pmol of isX001, 100 pmol of isX006, 0.05 mM dATP, $8.3 \times 10^{-10}$ mmol alpha-$^{32}$P-dATP (0.19 MBq), and approximately 5 units of DNA polymerase in 20 µl. The reaction was incubated at 37° C. for 1 hour. The reactions were loaded onto a 20% acrylamide gel comprising 7M urea and electrophoresed for approximately 1 hour and autoradiographed with no intensifying screen. The results confirmed that the DNA synthesis reaction yields similar amounts of product in the Tris-deficient reaction solution and in Tris-buffered reaction solutions.

Next, experiments were performed to determine the pH changes associated with DNA synthesis that are detected in the Tris-deficient reaction solution. First, to reduce further the Tris concentration in the reaction, Tris was removed from the commercial enzyme by dialyzing the enzyme in a solution that was the same as the enzyme storage solution except that it lacked Tris. An aliquot of the enzyme was concentrated by diafiltration. The enzyme was stored at 4° C. The dialyzed and concentrated Klenow exo polymerase was used in subsequent experiments.

Test reactions were assembled according to Table 2:

TABLE 2 pH measurement reactions

| Concentration | Constituent | Rxn D | Rxn E | Rxn F | 3.5x cocktail |
|---|---|---|---|---|---|
| 100 pmol/µl | isX001 | 10 µl | 10 µl | 10 µl | 35 µl |
| 100 pmol/µl | isX006 | — | 10 µl | — | 35 µl |
| 100 pmol/µl | isX003 | — | — | 10 µl | |
| 10x | DSC-D | 20 µl | 20 µl | 20 µl | 70 µl |
| 1 mM | dATP | 10 µl | 10 µl | 10 µl | 35 µl |
| ~5 U/µl | Klenow exo⁻ | 4 µl | 4 µl | 4 µl | 14 µl |
| | Water | 146 µl | 146 µl | 146 µl | 511 µl |
| | Extra Water | 10 µl | — | — | — |
| | Final Volume | 200 µl | 200 µl | 200 µl | 700 µl |

A pH meter was used to measure the pH of the reaction solution before and after each DNA polymerization reaction. pH readings were performed using an Accumet AB 15 pH meter with an Accumet microelectrode 1.5 stem (catalogue number 13-620-96). The Accumet pH sensor was used as a dependable model for both the i-STAT membrane pH electrode and the i-STAT mixed metal oxide pH electrode based on observations that the response characteristics of these sensors are substantially similar.

The pH was taken prior to incubation (Table 3, before reaction) and then after incubating the reactions at 37° C. for 1 hour (Table 3, after reaction). Table 3 shows that there is a significant pH change for the reaction using the isX006 template, which is expected to effect incorporation of the dATP at the end of the isX001 primer. The reaction with no primer shows a small positive pH change and the reaction with the isX003 primer, which is not expected to effect incorporation of the dATP into the isX001 primer, shows a small negative pH change. Accordingly, the results show that a change in pH (e.g., a pH change greater than 0.1) is indicative of nucleotide incorporation into a growing strand of DNA.

TABLE 3 measured pH changes

| pH | Rxn D | Rxn E | Rxn F |
|---|---|---|---|
| before reaction | 6.29 | 5.94 | 6.13 |
| after reaction | 6.37 | 5.57 | 6.03 |
| pH change | +0.08 | −0.37 | −0.1 |

All publications and patents mentioned in the above specification are herein incorporated by reference in their entirety for all purposes. Various modifications and variations of the described compositions, methods, and uses of the technology will be apparent to those skilled in the art without departing from the scope and spirit of the technology as described. Although the technology has been described in connection with specific exemplary embodiments, it should be understood that the invention as claimed should not be unduly limited to such specific embodiments. Indeed, various modifications of the described modes for carrying out the invention that are obvious to those skilled in pharmacology, biochemistry, medical science, or related fields are intended to be within the scope of the following claims.

We claim:

1. A device for determining the sequence of a nucleic acid, the device comprising a reaction vessel comprising a hydrogen ion-sensitive electrode in contact with a sample comprising the nucleic acid, wherein the hydrogen ion-sensitive electrode is either:
   a) a microfabricated metal oxide electrode comprising:
      i) an insulating material sensitive to hydrogen ions; and
      ii) a conductive metal oxide,
      wherein the microfabricated metal oxide electrode does not exhibit the bulk conductive properties of the conductive metal oxide; or
   b) a membrane electrode comprising:
      i) a photolithographic base layer; and
      ii) a hydrogen ion-sensitive membrane;
   wherein the nucleic acid coats the surface of the hydrogen ion-sensitive electrode.

2. The device of claim 1 further comprising a reference electrode.

3. The device of claim 1 wherein the reaction vessel is a cylinder having a diameter of approximately 200 μm or less and a height of approximately 30 μm or less.

4. The device of claim 1 wherein the hydrogen ion-sensitive electrode detects changes in pH greater than or equal to 0.1.

5. The device of claim 1 comprising a plurality of hydrogen ion-sensitive electrodes.

6. The device of claim 1 comprising a plurality of nucleic acids covering the hydrogen ion-sensitive electrode at a density equal to or greater than $2.2 \times 10^{10}$ molecules/cm$^2$.

7. The device of claim 1 wherein the insulating material has a density of hydrogen ion binding sites that is greater than $10^{13}$/cm$^2$.

8. The device of claim 1 wherein the insulating material is selected from the group consisting of tantalum oxide, zirconium oxide, and aluminum oxide.

9. The device of claim 1 wherein the conductive metal oxide is selected from the group consisting of iridium oxide, ruthenium oxide, platinum oxide, palladium oxide, rhodium oxide, and osmium oxide.

10. The device of claim 1 comprising a clonal plurality of nucleic acids.

11. The device of claim 1 wherein the hydrogen ion sensitive membrane comprises:
    a) a solvent mixture comprising cyclohexanone and propiophenone;
    b) sodium tetraphenylborate
    c) tridodecyl amine;
    d) dibutyl sebacate or o-nitrophenyloctylether; and
    e) high-molecular weight polyvinylchloride.

12. A system for sequencing a nucleic acid comprising:
    i) a device according to claim 1 comprising a cartridge and
    ii) a hand-held reading apparatus.

13. The system of claim 12 wherein the cartridge comprises:
    1) a hydrogen ion-sensitive electrode; and
    2) a first interface component configured to mate with the reading apparatus and communicate with the reading apparatus; and
    wherein the reading apparatus comprises:
    1) a second interface component configured to mate with the cartridge and communicate with the cartridge; and
    2) a microprocessor configured to receive data from the cartridge.

14. The system of claim 13 wherein the data is raw data or transformed data.

15. The system of claim 13 wherein the data indicates the presence of a medical condition in a subject.

16. The system of claim 13 wherein the data indicates the absence of a medical condition in a subject.

17. The system of claim 12 further comprising a user interface.

18. A method for determining the sequence of a nucleic acid, the method comprising:
    a) providing a reaction solution comprising:
        1) the nucleic acid;
        2) a polymerase; and
        3) an oligonucleotide complementary to the nucleic acid;
    b) adding a deoxynucleotide to the reaction solution; and
    c) monitoring the pH of the reaction solution using a device according to claim 1,
    wherein a change in the pH of the reaction solution indicates that the deoxynucleotide was polymerized to the 3' end of the oligonucleotide.

19. The method of claim 18 further comprising:
    d) removing the deoxynucleotide from the reaction solution or inactivating the deoxynucleotide.

20. A device for determining the sequence of a nucleic acid, the device comprising a reaction vessel comprising a hydrogen ion-sensitive electrode in contact with a sample comprising the nucleic acid, wherein the hydrogen ion-sensitive electrode is either:
    a) a microfabricated metal oxide electrode comprising:
        i) an insulating material sensitive to hydrogen ions; and
        ii) a conductive metal oxide,
        wherein the microfabricated metal oxide electrode does not exhibit the bulk conductive properties of the conductive metal oxide; or
    b) a membrane electrode comprising:
        i) a photolithographic base layer; and
        ii) a hydrogen ion-sensitive membrane;
    wherein the nucleic acid comprises a plurality of nucleic acids covering the hydrogen ion-sensitive electrode at a density equal to or greater than $2.2 \times 10^{10}$ molecules/cm$^2$.

* * * * *